US009545267B2

(12) United States Patent
Seifert et al.

(10) Patent No.: US 9,545,267 B2
(45) Date of Patent: Jan. 17, 2017

(54) LATERAL SPINOUS PROCESS SPACER

(75) Inventors: Jody L. Seifert, Birdsboro, PA (US); Luiz Pimenta, Sao Paolo (BR); Michael L. Boyer, II, Phoenixville, PA (US); David C. Paul, Phoenixville, PA (US)

(73) Assignee: Globus Medical, Inc., Audubon, PA (US)

( * ) Notice: Subject to any disclaimer, the term of this patent is extended or adjusted under 35 U.S.C. 154(b) by 732 days.

(21) Appl. No.: 11/691,357

(22) Filed: Mar. 26, 2007

(65) Prior Publication Data

US 2008/0243250 A1 Oct. 2, 2008

(51) Int. Cl.
A61B 17/70 (2006.01)
A61B 17/02 (2006.01)
A61F 2/30 (2006.01)

(52) U.S. Cl.
CPC ....... A61B 17/7062 (2013.01); A61B 17/7065 (2013.01); A61B 90/39 (2016.02); A61B 2017/0256 (2013.01); A61F 2002/3008 (2013.01); A61F 2250/0098 (2013.01)

(58) Field of Classification Search
CPC ...... A61B 17/7062–17/707; A61F 2/44–2/447
USPC ..................... 623/17.11–17.16; 606/246–249
See application file for complete search history.

(56) References Cited

U.S. PATENT DOCUMENTS

| 6,093,207 | A * | 7/2000 | Pisharodi | 623/17.16 |
| 6,673,075 | B2 | 1/2004 | Santilli | |
| 7,101,375 | B2 * | 9/2006 | Zucherman et al. | 606/249 |
| 7,753,938 | B2 | 7/2010 | Aschmann et al. | |
| 7,862,587 | B2 | 1/2011 | Jackson | |
| 7,963,991 | B2 * | 6/2011 | Conner et al. | 623/17.11 |
| 8,147,548 | B2 | 4/2012 | Zucherman | |
| 8,277,487 | B2 * | 10/2012 | Nishida | 606/249 |
| 2005/0113929 | A1 * | 5/2005 | Cragg | A61B 17/70 623/17.16 |
| 2005/0165398 | A1 * | 7/2005 | Reiley | 606/61 |
| 2005/0245937 | A1 * | 11/2005 | Winslow | 606/90 |
| 2006/0111715 | A1 | 5/2006 | Jackson | |
| 2006/0265066 | A1 * | 11/2006 | Zucherman et al. | 623/17.11 |
| 2006/0293662 | A1 * | 12/2006 | Boyer et al. | 606/61 |
| 2007/0032790 | A1 | 2/2007 | Aschmann | |
| 2007/0043361 | A1 * | 2/2007 | Malandain | A61B 17/025 606/262 |
| 2008/0108990 | A1 * | 5/2008 | Mitchell et al. | 606/61 |
| 2008/0161822 | A1 * | 7/2008 | Perez-Cruet | A61B 17/7065 606/99 |

FOREIGN PATENT DOCUMENTS

| EP | 1625835 A1 | 2/2006 | |
| WO | 2007018114 A1 | 2/2007 | |
| WO | WO2007018114 | * 2/2007 | A61F 2/44 |

OTHER PUBLICATIONS

"Generally," Merriam Webster dictionary, accessed May 29, 2014, www.merriam-webster.com/dictionary/generally.*

* cited by examiner

Primary Examiner — Jan Christopher Merene
Assistant Examiner — Steven Cotroneo

(57) ABSTRACT

In an exemplary embodiment, the present invention discloses interspinous process spacers that can be placed between adjacent spinous processes for minimally invasive surgical treatment of a spinal disease or defect. In particular, the present invention, in one embodiment, discloses an interspinous process spacer having a distraction end, a central support portion, and a trailing end. Also disclosed in the present invention are systems and kits including such implants, methods of inserting such implants, and methods of alleviating pain or discomfort associated with a spinal column disease or defect.

28 Claims, 16 Drawing Sheets

LATERAL SPINOUS PROCESS SPACER

FIELD OF THE INVENTION

The present invention is generally directed to intervertebral or interspinous process implants, systems and kits including such implants, methods of inserting such implants, and methods of treating spinal stenosis or for alleviating pain or discomfort associated with the spinal column.

BACKGROUND OF THE INVENTION

Occurrences of spinal stenosis are increasing as society ages. Spinal stenosis is the narrowing of the spinal canal, lateral recess or neural foramen, characterized by a reduction in the available space for the passage of blood vessels and nerves. Clinical symptoms of spinal stenosis include extremity pain, radiculopathy, sensory or motor deficit, bladder or bowel dysfunction, and neurogenic claudication. Pain associated with such stenosis can be relieved by surgical or non-surgical treatments, such as medication, physical therapy, back braces and the like. While spinal stenosis is generally more prevalent of the elderly, it can occur in individuals of all ages and sizes.

There is a need for implants that may be placed between spinal processes for minimally invasive surgical treatment of spinal stenosis.

SUMMARY OF THE INVENTION

Certain embodiments of the present invention are generally directed to minimally invasive implants, in particular, interspinous process implants or spacers. Other embodiments of the invention are further directed to systems and kits including such implants, methods of inserting such implants, and methods of alleviating pain or discomfort associated with the spinal column.

Some embodiments of the present invention provide spacers or implants and methods for relieving pain and other symptoms associated with spinal stenosis, by relieving pressure and restrictions on the blood vessels and nerves. Such alleviation of pressure may be accomplished in the present invention through the use of an implant placed between the spinous process of adjacent vertebra.

BRIEF DESCRIPTION OF THE DRAWINGS

The invention will be more readily understood with reference to the embodiments thereof illustrated in the attached figures, in which.

DETAILED DESCRIPTION OF THE INVENTION

Figure 1:
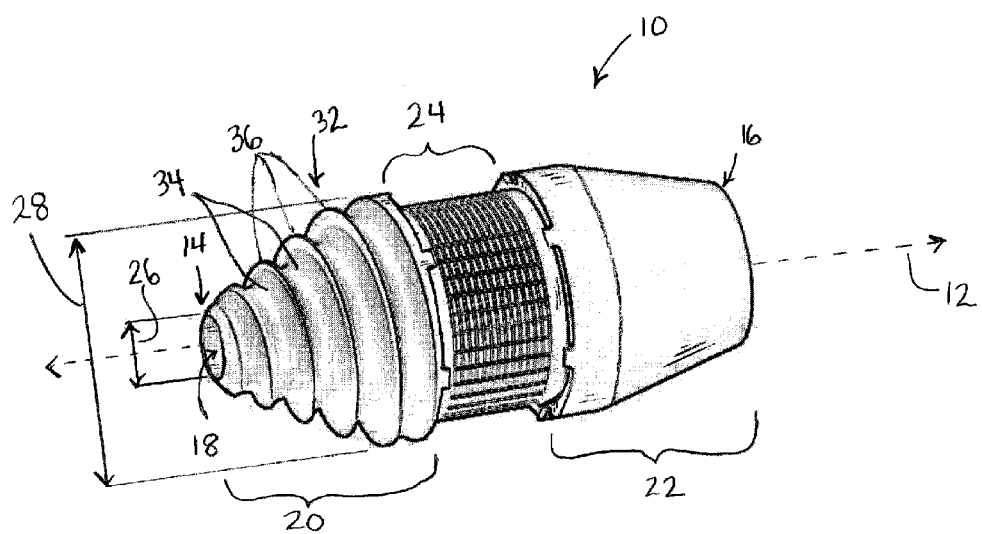
FIG. 1 is a perspective view of one embodiment of an implant according to the invention for creating, increasing, or maintaining distraction between adjacent spinous processes.

Embodiments of the invention will now be described. The following detailed description of the invention is not intended to be illustrative of all embodiments. In describing embodiments of the present invention, specific terminology is employed for the sake of clarity. However, the invention is not intended to be limited to the specific terminology so selected. It is to be understood that each specific element includes all technical equivalents that operate in a similar manner to accomplish a similar purpose.

Implants

Some embodiments of the present invention are directed to minimally invasive implants, in particular, interspinous process spacers. Implants in accordance with the invention may come in many shapes and sizes. The illustrative embodiments provided herein-below provide guidance as to the many types of implants that may be advantageously used in accordance with the present invention. In particular, the implants are adapted such that their insertion technique (including methods of the present invention) is minimally invasive, and generally simpler, and/or safer than those installed in open or more invasive techniques. According to one aspect, implants according to the present invention may be advantageously inserted into a patient as an out-patient procedure.

Embodiments of the present invention include implants adapted to be placed between first and second adjacent spinous processes. The implants may be adapted such that after insertion of an implant into a patient, a portion of the implant maintains a desired amount of distraction or spacing between two adjacent spinous processes. The implants or portions thereof that substantially maintain a desired spacing between spinous processes are also referred to herein as "spacers." In various embodiments described herein, the implants may include spinous process support surfaces, indented portions or saddle portions spaced apart by a distance (a) (FIG. 2), which generally corresponds to a desired distance for distraction or spacing of two adjacent spinous processes. Other embodiments similarly provide a desired distance for distraction or spacing of two adjacent spinous processes. Depending on the material and/or design of the implant, the desired distraction or spacing distance may vary somewhat after insertion, for example if a patient moves its spine into a position that causes further distraction. For example, in certain embodiments the implant may be resiliently compressible or expandable in the cranial-caudal direction such that the implant may support and or adjust to dynamic movement of the spine. Although not depicted in the figures discussed below, it is contemplated that embodiments of the present invention may be extended to provide distraction or spacing of more than two adjacent spinous processes.

Implants according to the present invention may be adapted to be inserted between a first and second spinous process at any region in the spine. Although typically implants according to the present invention may be inserted in the lumbar region, it is contemplated that it is possible to configure inserts according to the present invention for insertion into other regions such as for example, the thoracic or cervical region. In general, implants according to the invention may have varying profiles when viewed in a sagittal plane. In this regard, the implants can have varied cross-sectional shapes to conform to the varied anatomical shapes of the interspinous spaces of the spine.

Certain embodiments of implants of the invention may secure themselves in place without a supplemental attachment mechanism or fastening device attached directly to a spinous process or other portion of the spine. Alternatively, implants in accordance with the invention may be attached to one or more spinous processes or other portion of the spine, or may attach to itself in such a manner as to secure the implant between two adjacent spinal processes. By way of example, implants in accordance with the present invention may be attached to one or both spinous processes or other portion of the spine by one or more pins, screws, wires, cables, straps, surgical rope, sutures, elastic bands, or other fastening devices. Other exemplary implants, attachment mechanisms, and methods are disclosed in U.S. patent application Ser. No. 11/366,388, the entire contents of which are incorporated herein by reference. "Securing" implants between spinous processes, does not require that the implant not move at all, but rather means that the implant does not move so far away from between the spinous processes that it does not perform the function of maintaining a desired distraction distance or space between the adjacent spinous processes.

Implants in accordance with the present invention may be secured between spinous processes by methods other than using a fastening device. For example, according to certain embodiments, implants in accordance with the present invention may be secured in place with respect to spinous processes by mechanical forces resulting from the design of the implant, including the shape itself. Exemplary implants may also be secured to spinous processes, by surface modifications to portions of the implant, such as to create frictional forces or other bonds between the implant and spinous processes. Such surface modifications may include mechanical modifications to the surface (see e.g., protrusions 46 and/or knurling 47 in FIG. 2) and/or one or more coatings. Exemplary coatings which may be utilized include, but are not limited to, titanium plasma sprays and chrome sprays or the like. Such mechanical forces and/or surface modifications may be utilized in addition to, or in place of various other attachment methods described herein.

Figure 3:
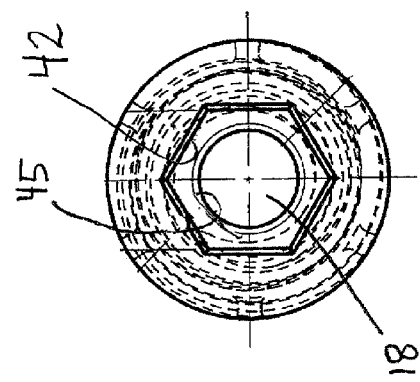
FIG. 3 is an end view of the implant of FIG. 1.
Figure 2:
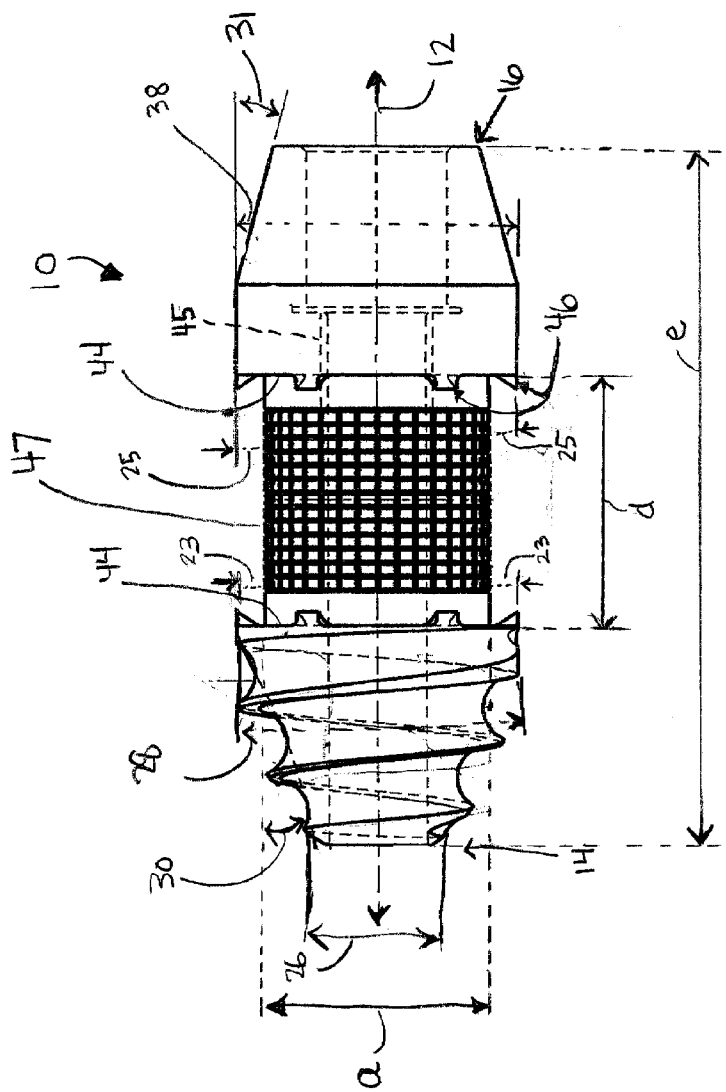
FIG. 2 is a side view of the implant of FIG. 1.
Figure 4:
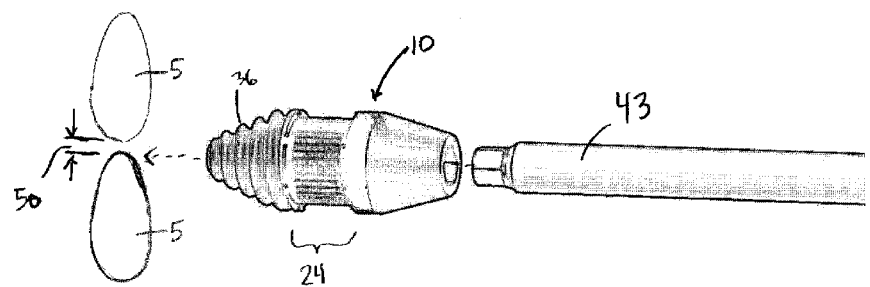
FIGS. 4-7 are side views demonstrating various steps according to one embodiment of a method of installation of the implant of FIG. 1.

Referring now to FIGS. 1-3, one exemplary embodiment of an implant 10 according to the invention is shown for creating, increasing, or maintaining distraction between adjacent spinous processes. In general, implant 10 is adapted and configured to be placed between adjacent spinous processes. For example, referring to FIGS. 24-25, a posterior and side view, respectively, of implant 10 is shown in implanted positions between to two adjacent spinous processes 5. As best seen in FIGS. 1-3, implant 10 generally comprises an elongate member extending laterally along axis 12 from a first lateral end 14 to a second lateral end 16.

In one embodiment, implant 10 may be cannulated with a central cannula or opening 18 extending along axis 12. One skilled in the art may appreciate that, in operation, cannulation 18 may facilitate advancement, travel, or delivery to an implant location over a guidewire. According to one embodiment, implant 10 may comprise a unitary body with a general barbell-like shape, and generally includes a first end portion or distraction portion 20 adjacent first end 14, a second end portion or trailing end portion 22 adjacent second end 16 and a central support portion or saddle portion 24 disposed between the distraction and trailing end portions 20, 22. As best seen in FIG. 2, support portion 24 may have a height (a) and width (d), and the implant may have an overall length (e). As best seen in FIG. 3, in one embodiment, implant 10 has a generally circular profile or perimeter when viewed perpendicular to axis 12. In alternate embodiments, however, implant 10 need not have a circular cross-sectional profile and the cross-sectional profile may vary along its length (e). For example, in one exemplary embodiment, distraction portion 20 may have a circular cross-sectional profile, and central support portion 24 may have a polyganol cross-sectional profile, and trailing end portion 22 may have a rectangular cross-sectional profile.

Distraction portion 20 is generally configured and dimensioned to facilitate lateral insertion between adjacent spinous processes. In one embodiment, distraction portion 20 generally comprises a frustoconical, wedged, or tapered shape widening along axis 12 from a minor diameter 26 adjacent the first end 14 to a major diameter 28 adjacent central support portion 24. In one exemplary embodiment, the distraction portion 20 is tapered along a cone angle 30 and cone angle 30 may be between about 1 and 65 degrees. In alternate embodiments, cone angle 30 may be between about 65 and 80 degrees. In one variation, distraction portion 20 may additionally include a ramped, toothed, fluted, threaded or grooved section 32. According to one embodiment, grooved section 32 generally comprises helical or spiral ramp peaks 36 extending from first end toward support portion 24. Ramp peaks 36 of section 32 may have a separation sufficiently narrow to prevent the adjacent spinous process from riding within the grooves 34 defined between the peaks 36. In this regard, the peaks 36 may be configured and dimensioned to engage or contact a portion of the spinous process bone and cause the implant 10 to advance or travel along axis 12 when implant 10 is rotated. In one variation, distraction portion 20 is configured and dimensioned such that when implant 10 is rotated about axis 12, the adjacent spinous processes ride upon ramp peaks 36 and are distracted or separated apart as implant 10 is advanced laterally along axis 12 during implantation. The rate at which the distraction occurs may be readily controlled by a surgeon by controlling the rate of rotation of implant 10, so that the surgeon may advance implant 10 along axis 12 as slow or as fast as desired. In this regard, implant 10 may be characterized as self-distracting, as the implant itself distracts or separates the spinous processes as it is being implanted, i.e. without requiring an additional distraction step or device.

Trailing end portion 22 adjacent second end 16 may comprise a generally frustoconical, wedged, or tapered shape narrowing along axis 12 from a major diameter 38 adjacent central support portion 24 to a minor diameter 40 adjacent the second end 16. Those skilled in the art will appreciate that such a tapered feature may be desirable to minimize wear and trauma with adjacent soft tissue and/or bone when implant 10 is installed in a patient. In one embodiment trailing end portion 22 is generally symmetrical to distraction portion 20 with generally similar lateral length, cone angle 31 and major and minor diameters, and in some embodiments may also include a spiral ramped section or any other toothed, fluted, threaded or grooved sections, similar to distraction portion 20. In alternate embodiments, however, the trailing end portion 22 need not be symmetrical whatsoever and may have any shape irrespective of the dimension of distraction portion 20. For example, in at least one alternate embodiment, angle 31 could be less or greater than cone angle 30 for distraction portion 20.

Figure 5:
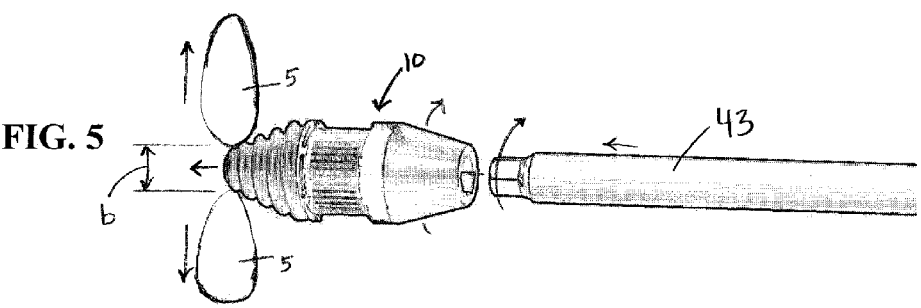
Figure 6:
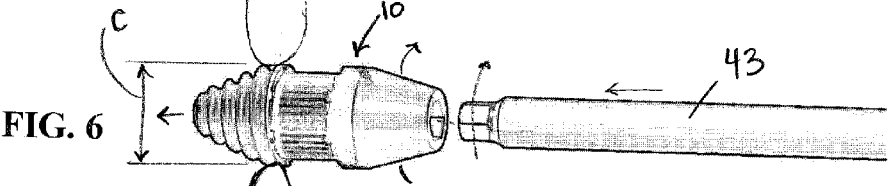
Figure 7:
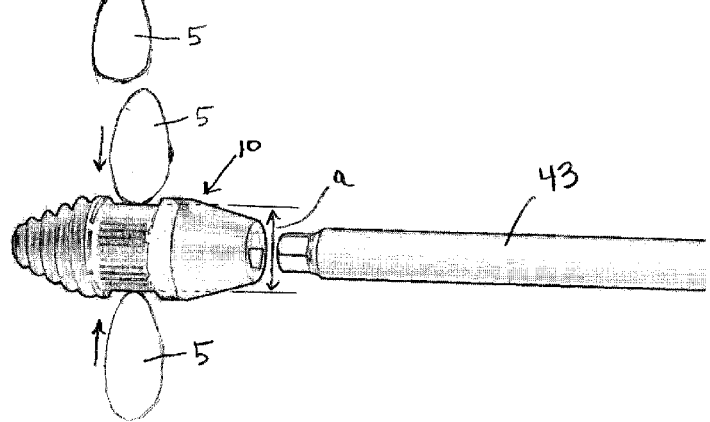

Referring to FIG. 3, in one embodiment, a hexagonal shaped socket or indentation 42 may be provided to receive an installation or driving tool such as a hexagonal shaped driver tool. One exemplary driving tool 43 constructed according to the invention is shown in FIGS. 5-7. In alternate embodiments, any other known rotational driving tools and engagement means may also be used, including but not limited to, a flat driver, a star shaped driver, or a threaded driver, among others. As best seen in FIG. 3, indent 42 may be concentric with cannula 18 to facilitate insertion with a cannulated driver tool over a guidewire extending through cannula 18 and indentation 42. In one variation, a threaded section 45 may be provided internal to indentation 42 to accommodate a threaded connection of an installation or removal tool (FIG. 26) with implant 10. In this regard, the threaded connection between a tool and the implant facilitates a laterally fixed relative connection between the implant and tool so that the implant does not dislodge from the trailing end and may efficiently transfer the rotational forces applied on the tool to the implant during installation. One skilled in the art may appreciate that the threaded connection may also facilitate the removal of implant 10 from the body of a patient should a surgeon so desire.

Central support portion 24 is provided between the distraction and trailing end portions 20, 22. In one embodiment, support portion 24 may have a diameter or height (a) less than the major diameters 28, 38 of portions 20, 22. In this regard, when viewed from the side, as seen in FIG. 2, implant 10 may appear to have a general H-like shape or a barbell-like shape, with the lateral sides 20, 22, being longitudinally spaced a distance 23, 25, respectively beyond central support portion 24. In one variation, distances 23, 25 do not need to be equal. According to one embodiment, lateral sides 20, 22 may be spaced a distance 23, 25 between about 1 mm and about 6 mm from the support portion 24. In one particular embodiment, distances 23, 25 is about 1 mm. In another embodiment, distance 23 is about 2 mm and distance 25 is about 3 mm.

As best seen in FIG. 2, in one embodiment, the transition from the distraction portion 20 to the central support portion 24 and the transition from the central support portion 24 to trailing end portion 22 may be abrupt. In this regard, a shoulder or generally vertical wall section 44 may be formed at either end of central support portion 24, and when implant 10 is implanted, wall sections 44 may serve to limit or block movement of the implant along axis 12 and/or dislodgement from the interspinous space. In alternate embodiments, the shoulder or transition from the central support portion 24 to the lateral end portions 20, 22 may be gradual, curved, or ramped and may server to center the adjacent spinous process within the support portion 24.

In one embodiment, textures, such as knurling 47, serrations, abrasions, or other similar features may be provided along the surface of central support portion 24 to facilitate gripping or frictional contact with bone, such as the spinous process, to limit or reduce movement and/or dislodgement from the interspinous space once installed. In one variation, one or more teeth or protrusions 46 may extend laterally inward from wall sections 44. Protrusions 46 may have a saw-tooth shape, have an angled undercut, or may have other sharpened end portions to grip and/or engage bone. In an alternate embodiment, protrusions 46 may comprise cylindrical spikes with sharp points. According to one variation, six protrusions 46 may be radially spaced about the perimeter of each wall section 44, however, in alternate embodiments more or less protrusions may be provided as desired. In some embodiments, the geometry and spacing of the protrusions may be varied between each wall or along an individual wall section 44. For example, a combination of saw-tooth shaped protrusions may be used in combination with spike shaped protrusions. In general, protrusions 46 may be configured and dimensioned to limit or reduce rotational, twisting, and/or lateral movement of implant 10 with respect to spinous processes when installed. In yet another embodiment, the wall sections 44 may have a star grind surface feature to limit rotational movement when installed. In other embodiments, one or more protrusions or spikes may be provided along central portion 24 and may extend radially outward to engage the spinous process.

In some embodiments, all or a portion of implant 10 may be resiliently compressible or expandable in the cranial-caudal direction such that the implant may support and or adjust to dynamic movement of the spine. For example, according to one embodiment, central support portion 24 may include a flexible bumper member to at least partially cushion the compression of adjacent spinous processes. In one variation, the bumper member may comprise a cylindrical sleeve provided to extend around the periphery of central support portion 24. In some embodiments, the bumper member may be integrated into the support portion and in alternate embodiments the bumper member may be fit over the support portion. In one variation, the bumper member may be made from a biocompatible polyurethane, elastomer, or other similar material. In still other embodiments, implant 10 may be made from varying materials along its length, such that for example the central support portion may be made from a resilient material, such as polyurethane, elastomer or the like, and the end portions may be made from a rigid material, such as titanium or the like.

The implant itself may serve to dilate or distract the spinous processes as it is being inserted and/or after insertion. For example, in embodiments in which the implant is similar to that depicted in FIGS. 1-3, the first end 14 of implant 10 may be initially inserted or advanced laterally between compressed adjacent spinous processes as shown in FIGS. 4-7, for example. The supraspinous ligament may or may not be removed. In an initial pre-implantation condition, shown in FIG. 4, the adjacent spinous processes 5 may be compressed or narrowly spaced such that the initial space or longitudinal distance 50 between the processes may be about equal to or slightly larger or smaller than distance (b) of implant 10. During lateral insertion of the implant, one or more ramp surfaces or portions of the implant may contact one or both of the spinous processes 5 and may initially distract the processes a distance (b). As the implant is rotated, the ramp peaks 36 draw the implant 10 further between the spinous processes and, the wedged or tapered shape of the distraction portion may distract the spinous processes further apart from one another, until the implant is rotated and advanced laterally into an implanted position (FIGS. 11-12) and the spinous processes are fitted into the central support portion 24 of the implant 10. In operation, the ramp surfaces engage the adjacent spinous processes as the implant is rotated to act or perform in a cam-like manner to translate the rotational force to separate the spinous processes in the longitudinal or cranial-caudal direction as the implant is rotated. The maximum distraction of spinous processes by the implant 10 is distance (c) depicted in FIG. 6. According to one embodiment, distance (c) is greater than distance (a) such that the spinous processes 5 may be slightly "over distracted" during installation. In this regard, one skilled in that art may appreciate that such an over distraction may facilitate enhanced tactile feedback to a surgeon during installation as the spinous processes drop into the central support portion to signify a desired lateral placement in the patient with the spinous processes positioned within the central support portion. Once the implant is implanted and after the spinous processes are fitted into the central support portion 24, the implant may maintain the spinous processes in a distracted or spaced condition, for example where the distance (a) of the implant is greater than a pre-implantation distance between the spinous processes.

Figure 8:
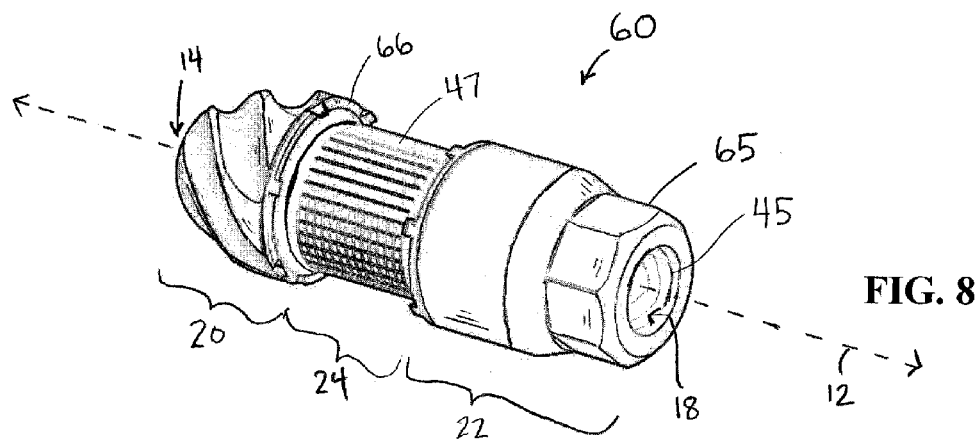
FIGS. 8-9 are front and rear perspective views of another embodiment of an implant according to the invention.
Figure 9:
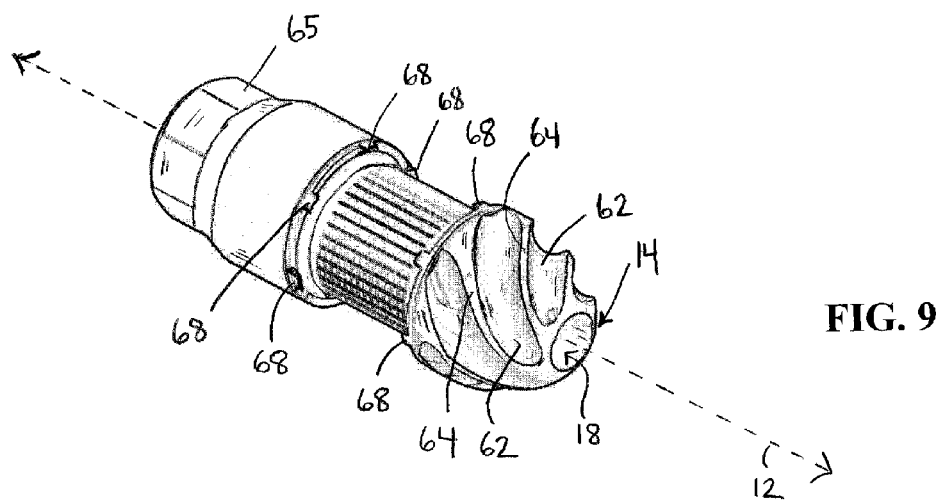
Figure 10:
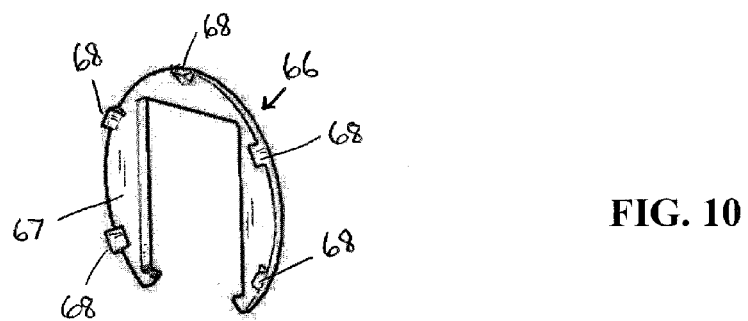
FIG. 10 is a perspective view of one embodiment of a ring attachable to the implant of FIGS. 8-9.

Referring to FIGS. 8-10, another embodiment of an interspinous process implant 60 is shown. Implant 60 is similar to implant 10 described above, however, in this embodiment, the distraction portion 20 comprises a plurality of spiral grooves or flutes 62 disposed about axis 12 and extending from a narrow first end 14 toward central support portion 24. In this embodiment, generally sharp peaks or ridges 64 may be formed along the edge of the flutes 62 and generally positioned at an angle with a plane perpendicular to axis 12 to form an inclined ramp. The ridges 64 are configured and dimensioned to engage or contact a portion of the spinous process bone and when implant 60 is rotated about axis 12, ridges 64 generally cause the implant to advance or travel along axis 12. In this embodiment, flutes 62 extend in a spiral direction to facilitate insertion of implant 60 in a "quarter rotation technique" such that a surgeon may insert implant 60 by rotating the device one fourth of a revolution or ninety degrees. In this regard, in one embodiment, each ridge 64 extends one fourth of the way around the periphery of distraction portion 20. In alternate embodiments, each ridge 64 may extend one half, three fourths, or any other fractional distance around the periphery as desired to facilitate a corresponding fractional rotation insertion technique. According to one embodiment, six flutes are provided, however, in alternate embodiments, more or less spiral flutes may be used.

Referring to FIG. 8, according to one embodiment of the invention, implant 60 may have a trailing end portion 22 with an external hexagonal shaped portion 65 instead of an internal hexagonal socket or indentation 42 as described above. Like indentation 42, hexagonal portion 65 may be provided to engage an installation tool such as a hexagonal socket shaped driver tool. As described above with respect to implant 10, in alternate embodiments any other known rotational driving tools and engagement means may also be used. Also similar to indentation 42 described above, in one embodiment, a threaded section 45 may be provided to accommodate a threaded connection of an installation or removal tool (FIG. 26) with implant 60. In this regard, the threaded connection between the tool and the implant facilitates a laterally fixed relative connection between the implant and tool so that the implant does not dislodge from the trailing end and may efficiently transfer the rotational forces applied on the tool to the implant during installation. One skilled in the art may appreciate that the threaded connection may also facilitate the removal of implant 60 from the body of a patient should a surgeon so desire.

Referring to FIGS. 8-10, according to another aspect, embodiments of implants according to the invention may comprise a separate protrusion ring 66 that may be snap fitted around central support portion 24. As best seen in FIG. 10, protrusion ring 66 may comprise a thin C-shaped body 67 with a plurality of protrusions 68 extending laterally from one side. Protrusions 68 may be similar to protrusions 46 described above and are generally radially spaced around the perimeter of body 67. In one variation, body 67 of ring 66 has an opening 69 to facilitate insertion over implant 60 adjacent the lateral sides of central support portion 24 with the protrusions facing laterally inward as depicted in FIGS. 8-9. Protrusions 68 may be configured and dimensioned to limit or reduce rotational, twisting, and/or lateral movement of implant 60 with respect to spinous processes when installed. In this embodiment, ring 66 and implant 60 may be made from different materials. For example, according to one embodiment, implant 60 may be made from a radiolucent material, such as PEEK, and the ring(s) 66 may be made from a radio-opaque material, such as titanium, tantalum or any other suitable material known to those skilled in the art. In this regard, the ring(s) 66 may serve a dual purpose as a marker device recognizable under fluoroscopy as well as serving the function of limiting or reduce rotational movement when installed. In alternate embodiments, rings 66 may be provided that are entirely free of protrusions or that may sit within grooves of central support portion 24 and could function solely as marker devices without limiting movement of implant 60 relative to spinous processes when installed. For example, in one alternative embodiment, a pair of rings 66 may be provided on either lateral side of support portion 24 to provide visual markers under fluoroscopy indicating the width of support portion 24 to facilitate alignment of implant 60 with the spinous process(es) when installed. Similarly, a surgeon may visualize the central openings and/or perimeter of rings 66 under lateral fluoroscopy to gauge the lateral alignment with the spinous process(es) when installed.

Figure 11:
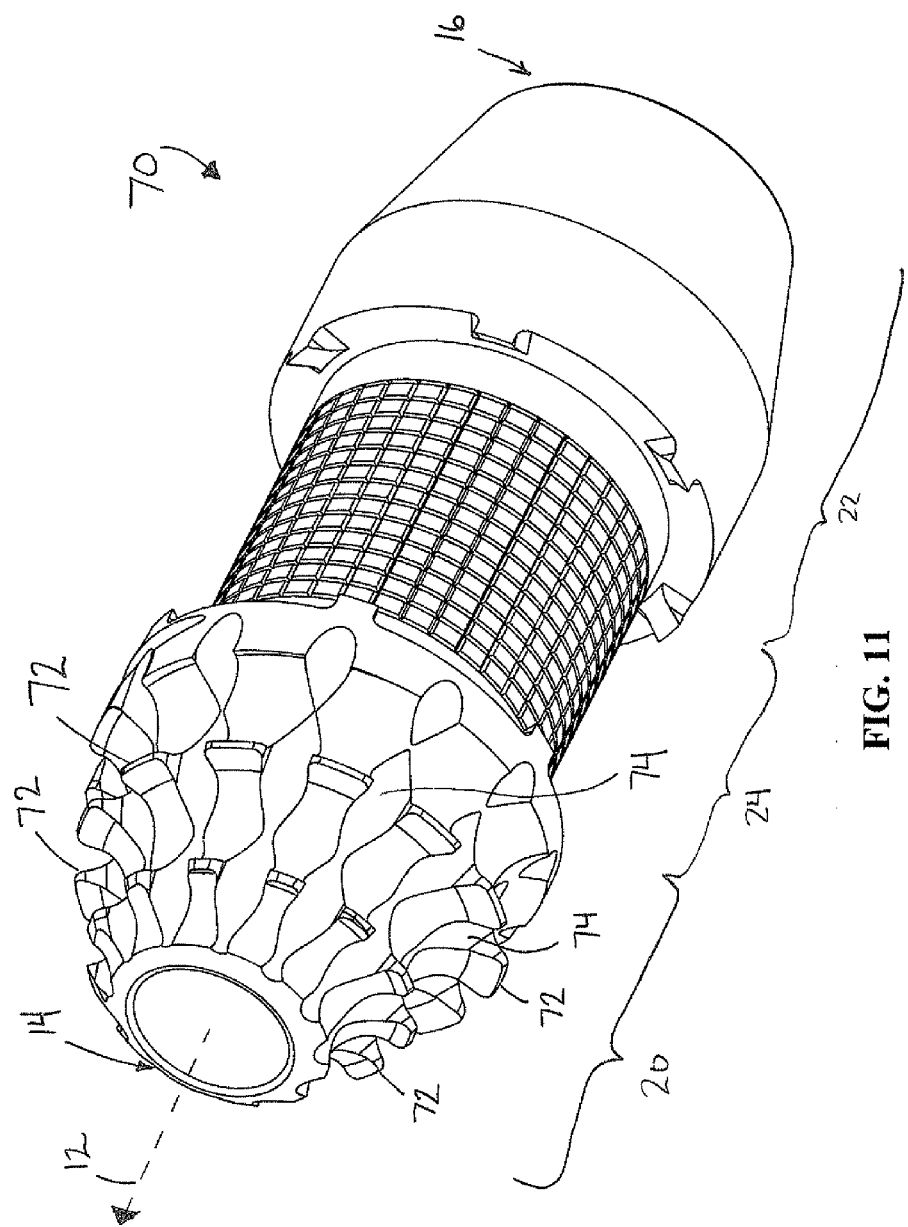
FIG. 11 is a front perspective view of another embodiment of an implant according to the invention.

Referring to FIG. 11, another embodiment of an interspinous process implant 70 is shown. Implant 70 is similar to implants 10, 60 described above, however, in this embodiment the distraction portion 20 comprises a plurality of laterally spaced rows of outwardly protruding teeth 72 disposed about axis 12 and spaced from a narrow first end 14 to a central support portion 24. In this embodiment, the individual teeth 72 are radially spaced apart by a laterally extending groove or flute 74. As can be seen in FIG. 11, the teeth 72 nearer first end 14 are generally narrower than teeth 72 adjacent central support portion 24. In one variation, teeth 72 extend at an angle with a plane perpendicular to axis 12 to form an inclined ramp segment. The teeth 72 are configured and dimensioned to engage or contact a portion of the spinous process bone and when implant 70 is rotated about axis 12, teeth 72 cause the implant to advance or travel along axis 12.

Figure 12:
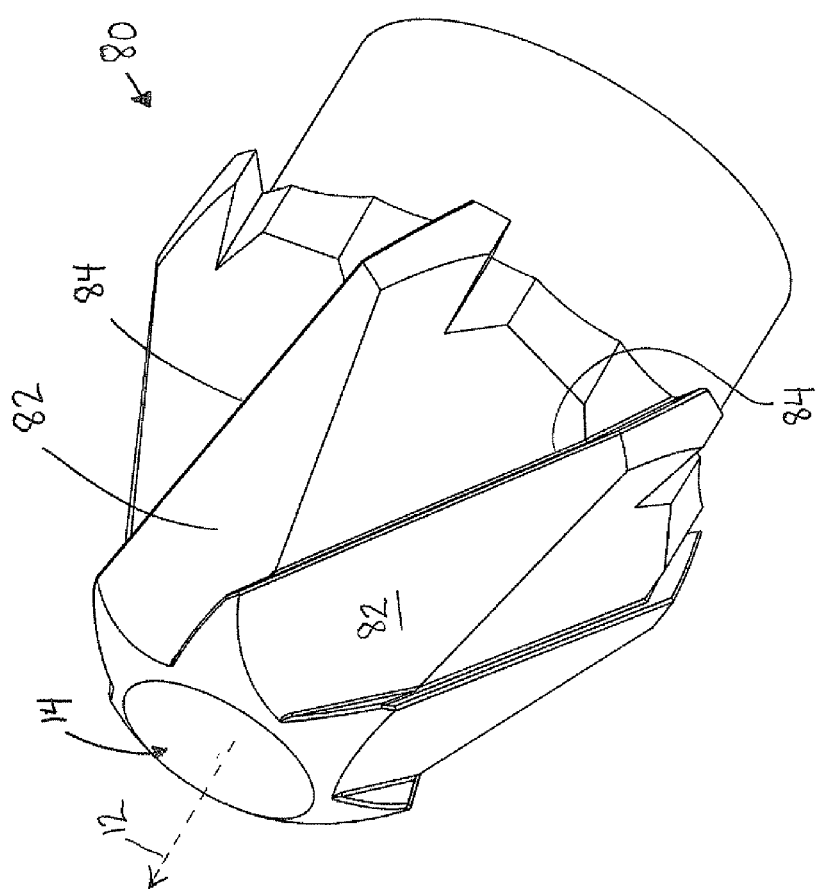
FIG. 12 is a partial front perspective view of another embodiment of an implant according to the invention.

Referring to FIG. 12, another embodiment of an interspinous process implant 80 is shown. Implant 80 is similar to implants 10, 60 described above, however, in this embodiment, the distraction portion 20 comprises a plurality of flat facetted surfaces 82 radially disposed about axis 12 and extending angularly from a narrow first end 14 to a maximum diameter adjacent central support portion 24. In this embodiment, sharp edges or ridges 84 may be formed along the edge of the facet surfaces 82 at an angle with a plane perpendicular to axis 12 to form an inclined ramp. In this embodiment, surfaces 82 generally extend the entire length of distraction portion 20 and ridges 84 generally form a linear path from the first end toward the central support portion. The ridges 84 are configured and dimensioned to engage or contact a portion of the spinous process bone and when implant 80 is rotated about axis 12, ridges 84 cause the implant to advance or travel along axis 12.

Figure 13:
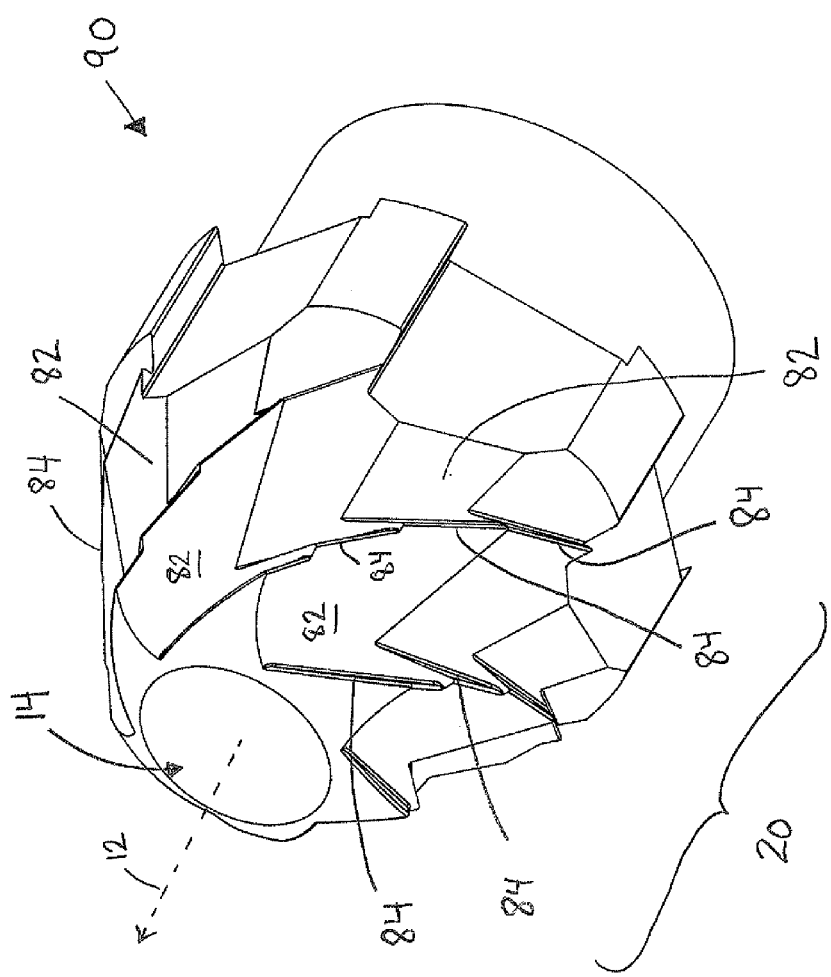
FIG. 13 is a partial front perspective view of another embodiment of an implant according to the invention.

Referring to FIG. 13, another embodiment of an interspinous process implant 90 is shown. Implant 90 is similar to implant 80 described above, however, in this embodiment the flat facetted surfaces 82 radially disposed about axis 12 are staggered, twisted or stepped angularly from a narrow first end 14 to a maximum diameter adjacent central support portion 24. A plurality of flat surface segments 82 extend the length of distraction portion 20 and ridges 84 generally form a series of linear segments along a path from the first end toward the central support portion. Similar to implant 80 described above, the ridges 84 are configured and dimensioned to engage or contact a portion of the spinous process bone and when implant 80 is rotated about axis 12, ridges 84 cause the implant to advance or travel along axis 12. In this variation, a surgeon implanting the device during surgery may experience enhanced tactile feedback due to the segmented ridges. For example, during insertion a surgeon may be able to count the clicks or segment rotations to monitor the progress of the insertion.

Figure 14:
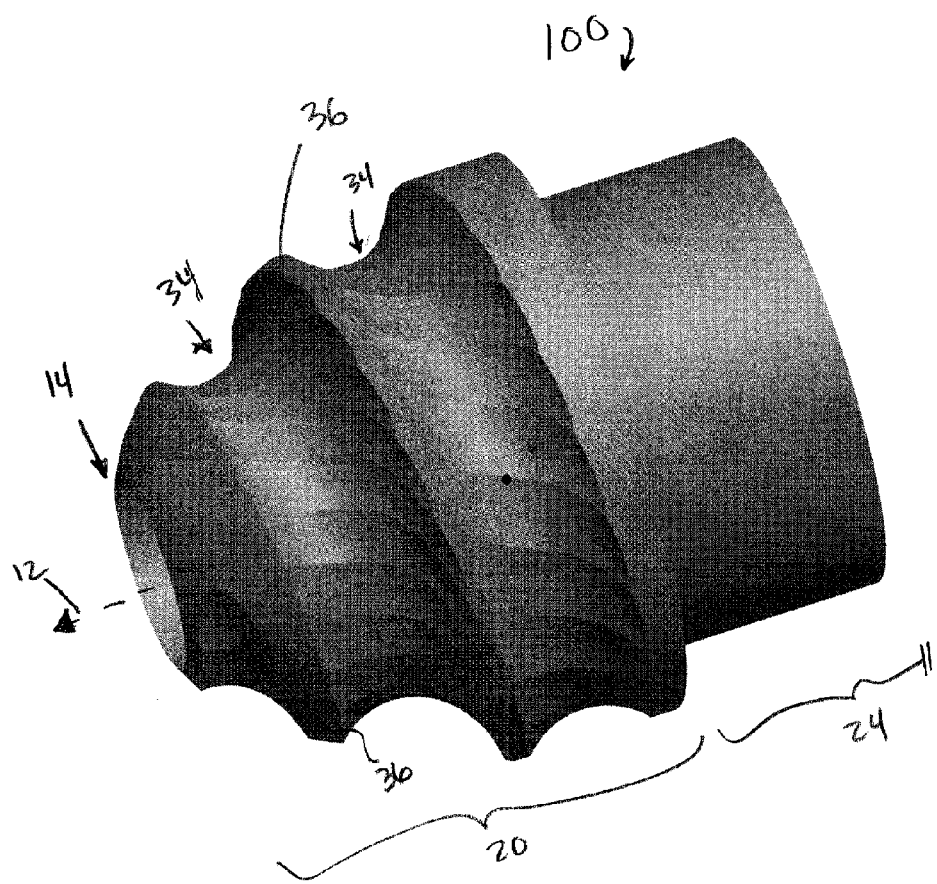
FIG. 14 is a partial front perspective view of another embodiment of an implant according to the invention.

Referring to FIG. 14, another embodiment of an interspinous process implant 100 is shown. Implant 100 is similar to implant 10 described above, however in this embodiment the spiral ramp grooves 34 and peaks 36 are segmented or less smooth along their path. Similar to implant 10 described above, the peaks 36 are configured and dimensioned to engage or contact a portion of the spinous process bone and when implant 100 is rotated about axis 12, peaks 36 cause the implant to advance or travel along axis 12. In this variation, like implant 90 described above, a surgeon implanting the device during surgery may experience enhanced tactile feedback due to the segmented peaks 36. For example, during insertion a surgeon may be able to count the clicks or segmental advancement to monitor the progress of the implant insertion.

Figure 15A:
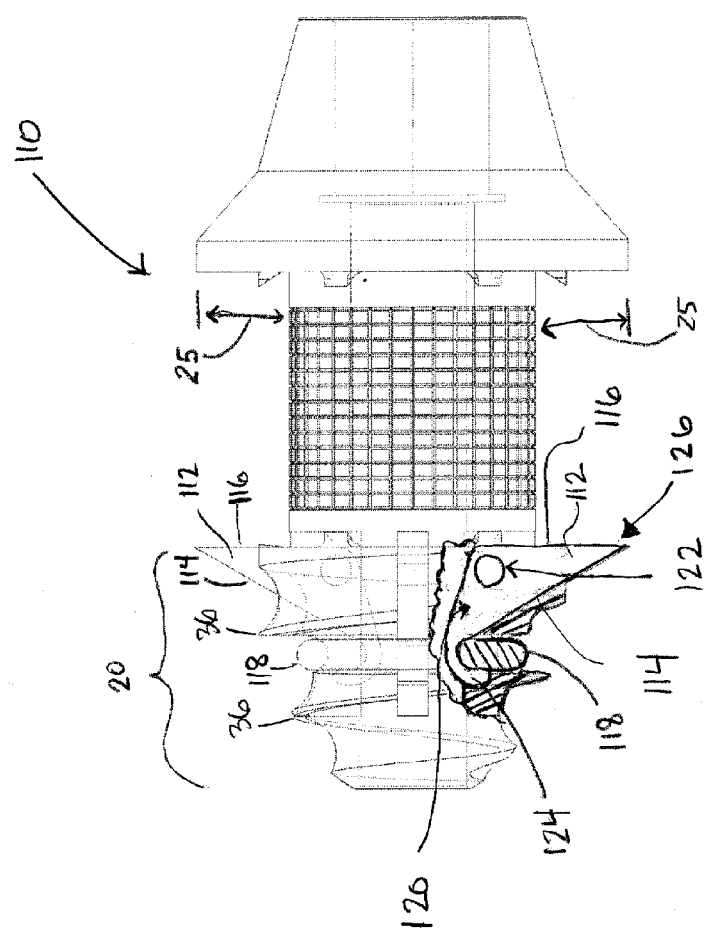
FIG. 15A is a partial cross-sectional side view of another embodiment of an implant according to the invention.
Figure 15B:
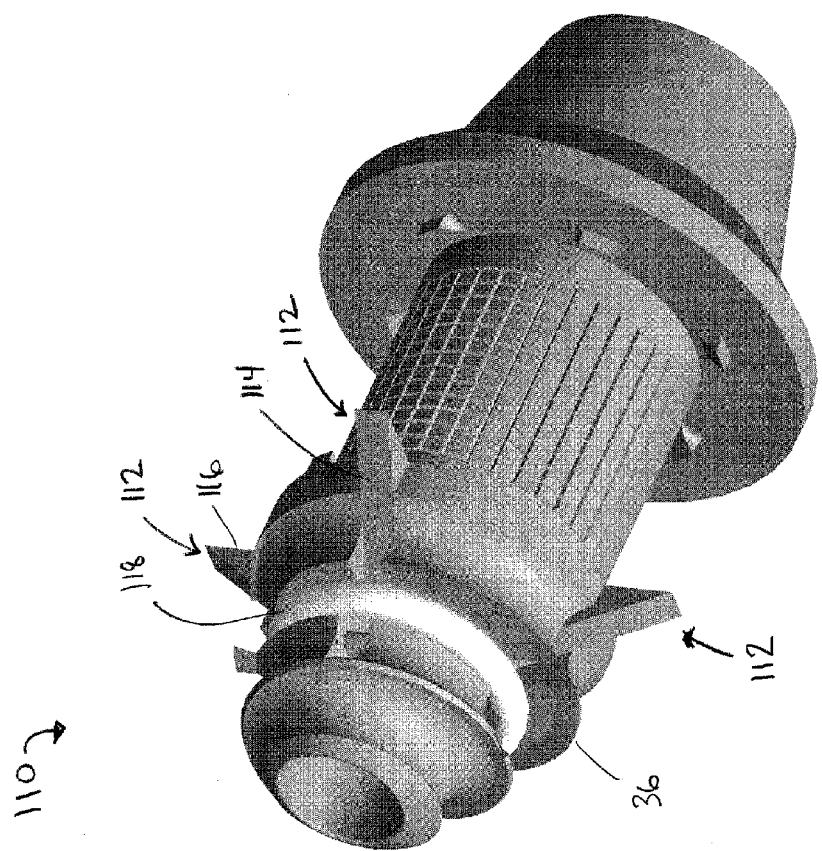
FIG. 15B is a perspective view of the embodiment of FIG. 15A.

Referring to FIGS. 15A-B, another embodiment of an interspinous process implant 110 is shown. Implant 110 is similar to implant 10, described above, however, in this embodiment the distraction portion 20 comprises a plurality of wing members 112 disposed about axis 12. Wing members 112 are moveable from a first position to a second position, shown in FIGS. 15A-B. During installation, wing members 112 are configured to remain in a first position below the profile of peaks 36 such that when implant 110 is implanted, the spinous processes are distracted in a similar manner as described above with respect to implant 10. When implant 110 is installed in an implanted position, wing members 112 may be selectively moved into a second position, as shown in FIGS. 15A-B, wherein the wing members 112 generally protrude or extend radially beyond peaks 36. In this regard, according to one embodiment, wing members 112 may have a tapered first side 114 and a generally flat second side 116. Wings 112 may be attached to implant 110 such that when in a second position, second side 116 is generally perpendicular to support portion 24 to create a larger lateral barrier, wall, or blocking portion adjacent central support portion 24. According to one variation, wing members 112 may be biased toward the second position by a biasing member, such as an O-ring 118. As best seen in FIG. 15A, in this variation, each wing member 112 may comprise a cantilevered body or pivot arm 120 pivotable about a pivot point 122 and the O-ring 118 may apply a radially inward biasing force to a tail portion 124 of one side of the wing body 120 to cause an opposite tip portion 126 of each wing member 112 to pivot about point 122 toward the second position. When implant 110 is advanced over a guidewire, the guidewire extends within the central cannula and contacts the tail portion 124 of each wing member and the tail portion 124 is forced radially outward, forcing the tip portion 126 to pivot inward toward the first position. One skilled in the art may appreciate that utilizing such a configuration, the wing members 112 may remain in a first position to facilitate implantation over a guidewire and then once the guidewire is removed, the wing members may spring or bias outwards to the second position to form a larger lateral barrier, wall, or blocking portion adjacent central support portion to limit or reduce the possibility of lateral migration of implant 110 in the body. In alternate embodiments, alternative mechanisms may be utilized to achieve the aforementioned result. For example, in one alternative a torsion spring may be positioned adjacent pivot point 122 to bias the wing members 112 toward the second position. Also, in alternative embodiments, the shapes and dimensions of wing members may be altered as desired.

Kits having at least one implant such as those depicted in FIGS. 11-15, may include various sizes of implants having varying heights (a), widths (d), and overall lengths (e), for example having variations with incremental distances. In one embodiment, a system or kit may be provided that has implants having heights (a) between about 6 mm to about 22 mm. For example, in one variation implants having heights (a) of 8 mm, 10 mm, 12 mm, 14 mm, 16 mm, 18 mm, and 20 mm may be provided. In another variation, a system or kit may be provided that has implants having widths (d) between about 6 mm to about 18 mm. For example, in one variation implants having widths (d) of 8 mm, 12 mm, and 16 mm may be provided. In yet another variation, a system or kit may be provided that has implants having overall lengths (e) between about 20 mm and about 60 mm. For example, in one variation implants having overall lengths (e) of 25 mm and 50 mm may be provided.

Material

Implants in accordance with the present invention may be made of one or more materials suitable for implantation into the spine of a mammalian patient. Materials in accordance with the present invention may be biocompatible with a mammalian patient and/or may have one or more surface coatings or treatments that allow the spacers to be biocompatible. Materials in accordance with the present invention may include one or more materials having sufficient load capability and/or strength to maintain the desired spacing or distraction between spinous processes. Depending on the design employed, certain embodiments may have components or portions made of a material having certain flexibility, as desired for the particular application. Additionally, the materials of the present invention may be made of one or more materials that maintain their composition and shape for as long a time as possible without degrading or decomposing or changing shape, such that replacement of the implant is avoided.

Suitable materials for use in accordance with the present invention would be known to those skilled in the art. Non-limiting examples include one or more materials selected from medical grade metals, such as titanium or stainless steel, biocompatible polymers, such as polyetheretherketone (PEEK), ceramics, deformable materials, bone, allograft, demineralized or partially demineralized bone, allograft ligament, and polyurethane (for example, for portions of the insert where cushioning is desired). Similarly, any fastening devices may be made of materials having one or more of the properties set forth with respect to the implant itself. For example, screws or pins may include titanium and straps may include polyethylene. In some embodiments, primarily radiolucent material may be used. In this regard, radio-opaque material or markers may be used in combination with the radiolucent material to facilitate implantation. Exemplary radio-opaque material includes but is not limited to titanium alloys, tantalum or other known radio-opaque marker material. As indicated above, implants in accordance with the present invention may have one or more portions that may have modified surfaces, surface coatings, and/or attachments to the surface, which may assist in maintaining the spacer in a desired position, for example by friction. Suitable surface modifications, coatings, and attachment materials would be known to those skilled in the art, taking into consideration the purpose for such modification, coating, and/or attachment.

Methods for Treating Stenosis and Methods of Inserting an Implant

Methods are provided for treating spinal stenosis. Methods are also provided for inserting an implant. These methods may include implanting a device to create, increase, or maintain a desired amount of distraction, space, or distance between adjacent first and second spinous processes. The adjacent first and second spinal processes may be accessed by various methods known by practitioners skilled in the art, for example, by accessing the spinous processes from at least one lateral side/unilateral, bilateral, or midline posterior approach.

Certain methods of the present invention include creating an incision in a patient to be treated, dilating any interspinous ligaments in a position in which the implant is to be placed in the patient, sizing the space between adjacent spinous processes (for example using trials), and inserting an implant of the appropriate size between the adjacent spinous processes. Methods of the present invention may include securing the implant to one or more of the spinous processes, to one or more other portions of the patient's spine, and/or to itself such that the implant maintains its position between the spinous processes.

Methods of the present invention may include dilating or distracting the spinous processes apart from one another before sizing and/or before inserting the implant. Methods may vary depending on which implant is being inserted into a patient. For example, certain implants may require distracting the spinous processes apart before inserting the implant, while other implants may themselves dilate or distract the spinous processes while inserting the implant. In embodiments where the implants themselves dilate or distract the spinous process, the implant may have, for example, a predetermined shape to dilate, distract, or otherwise move or separate apart adjacent spinous processes such as a cam or cam-like profile, it may have a distraction device that is deployed, and/or it may have a tapered expander to distract an opening between the adjacent spinous processes or other features to facilitate distraction of the adjacent spinous processes.

According to certain embodiments, spacers may be placed between the spinous processes anterior to the supraspinous ligament, avoiding the nerves in the spinal canal. The procedure may be performed under local anesthesia. For surgical procedures, in which an implant is being inserted into the lumbar region, the patient may be placed in the right lateral decubitus position with the lumbar spine flexed or in another flexed position. According to one method, a surgeon may desire to use fluoroscopy to align in parallel the adjacent vertebral bodies corresponding to the adjacent spinous processes to gauge the desired distraction distance.

According to certain embodiments, one or more probes may be used to locate the space between the spinous processes. Depending on the design of the spacer to be inserted, the space may be widened, for example with a dilator before inserting the implant.

Figure 16:
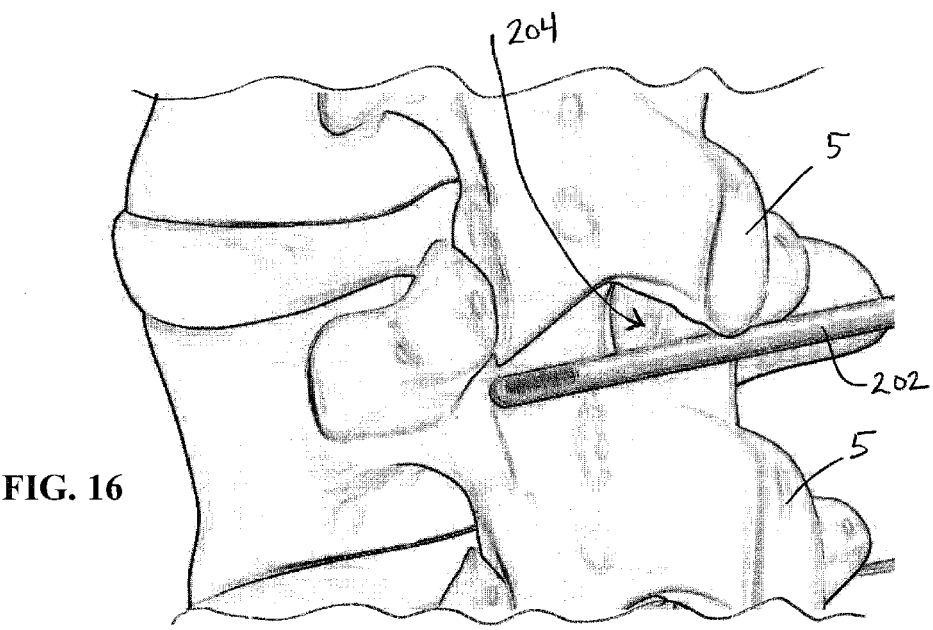
FIGS. 16-23 are perspective views demonstrating various steps according to one embodiment of a method of installation of the implant of FIG. 1.
Figure 17:
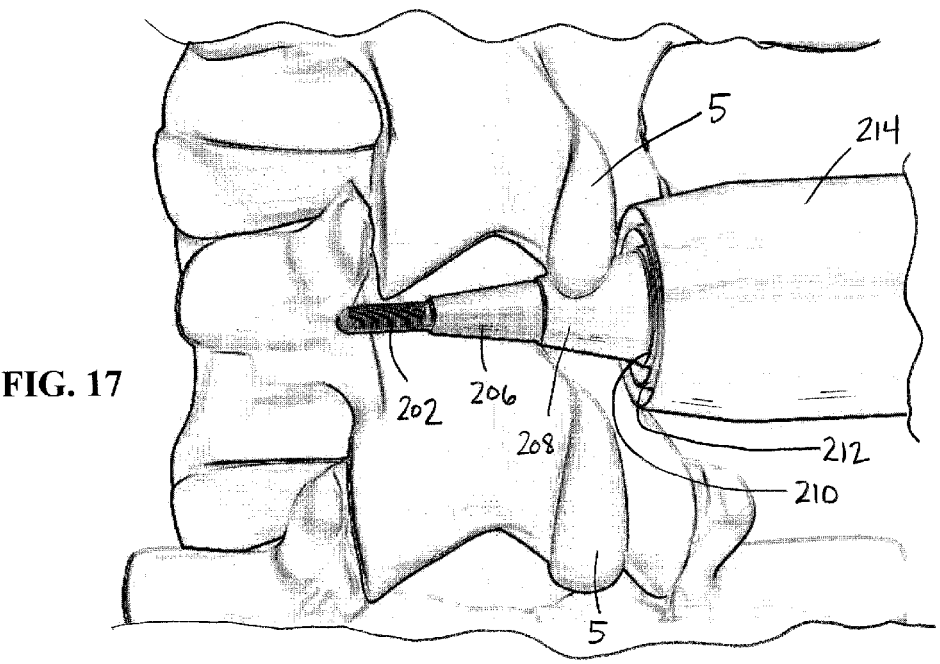
Figure 18:
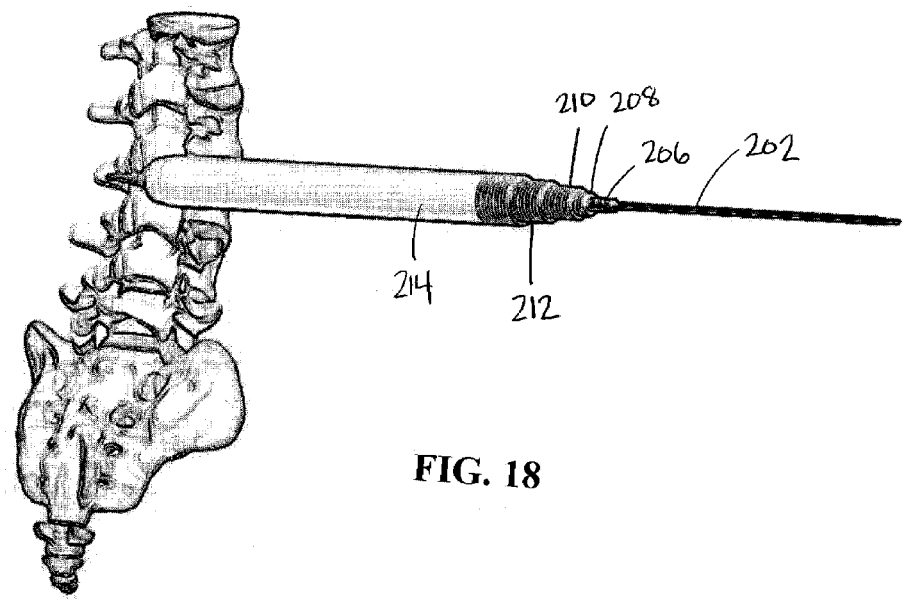
Figure 19:
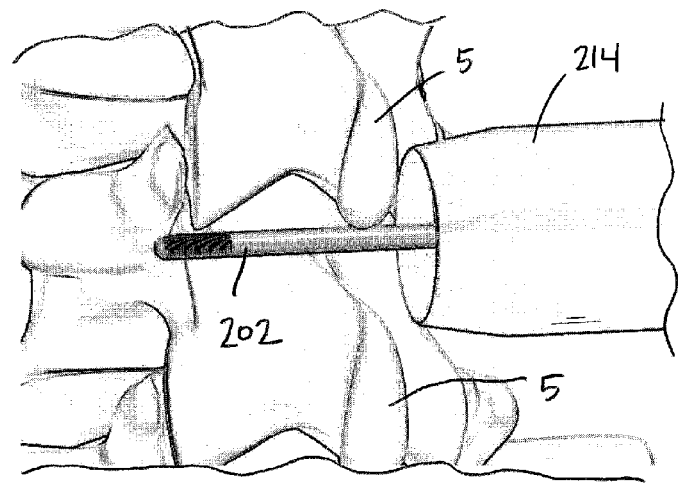
Figure 20:
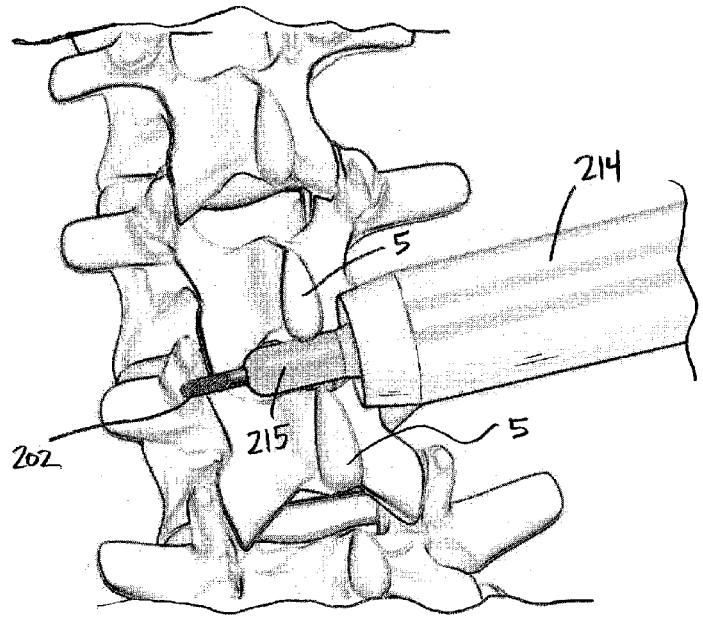
Figure 21:
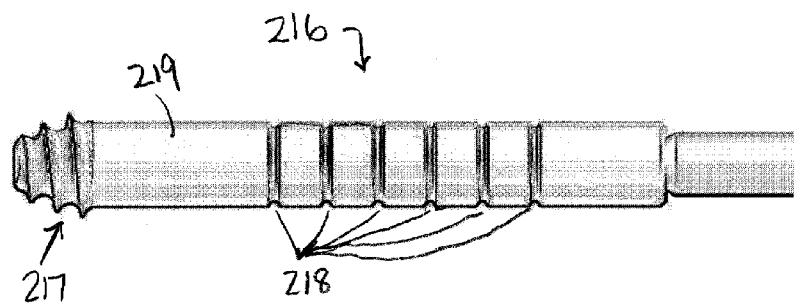

Referring to FIGS. 16-25, one embodiment of a surgical method according to the invention for implanting an implant 10 in the spine is disclosed. According to this embodiment, the adjacent first and second spinal processes 5 may be accessed from one lateral side through a minimally invasive procedure. In this regard, according to certain methods of the invention, a unilateral approach may be used to install implant 10 without removal of the supraspinous ligament. In this method, as shown in FIG. 16, a guide wire 202, such as a K wire, is inserted laterally through the skin and into the interspinous space 204. According to one method, a working portal may be created concentric to the guidewire 202, as shown in FIGS. 17-18, by inserting a series of sequentially larger diameter tubes 206, 208, 210, 212, 214 to dilate the tissue surrounding guidewire 202. Referring to FIG. 19, once a dilating tube having a sufficiently large inner diameter to accommodate implant 10 is positioned about guidewire 202, the smaller diameter tubes 206, 208, 210, 212 may be withdrawn, leaving the guidewire 202 and the outer tube 214. Referring to FIG. 20, one or more trials 215 may then be inserted to appropriately size the interspinous space 204 and the trials 215 may also be utilized to dilate interspinous ligaments. In one exemplary embodiment, a generally cannulated cylindrical trial 215, shown in FIG. 20, may be utilized to size the space between adjacent processes 5. Referring to FIG. 21, an alternate embodiment of a trial 216 that may be used is shown which may comprise a ramped tip portion 217 adjacent its distal end and multiple longitudinal indentations or markings 218 on at least a portion of central portion 219 and may provide visual indication when viewed under fluoroscopy of the width of the spinous processes and facilitate the surgeon's selection of an appropriately sized implant. Similarly, the appropriate diameter of central portion 219 of trial 216 may be selected to gauge the amount of distraction desired. In this regard, the spacing of the spinous processes may be viewed under fluoroscopy to facilitate the surgeon's selection of an appropriately sized implant. Finally, an implant of the appropriate size may be inserted between the adjacent spinous processes.

Figure 22:
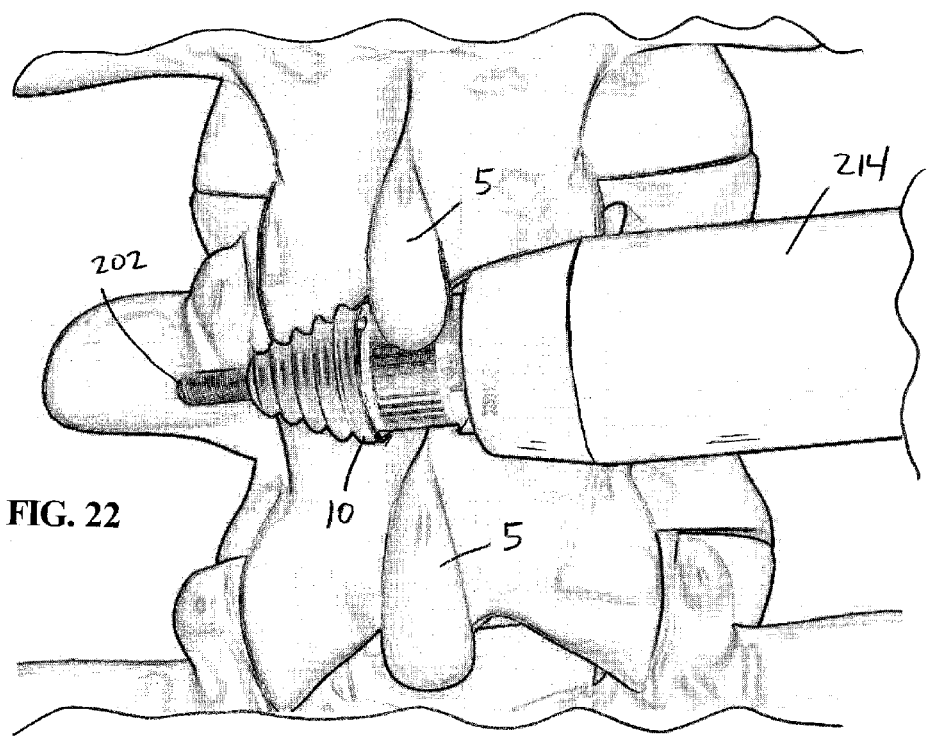
Figure 23:
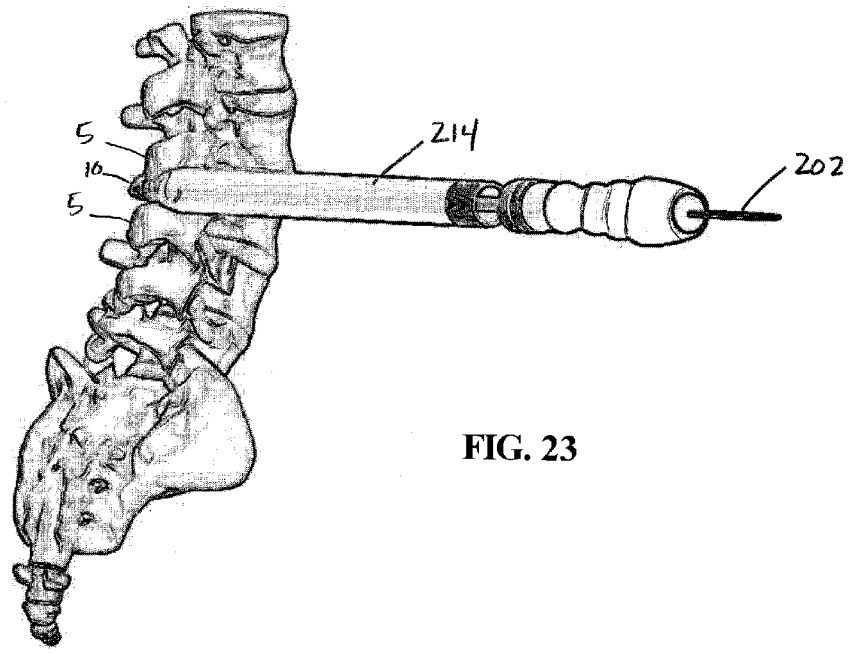
Figure 24:
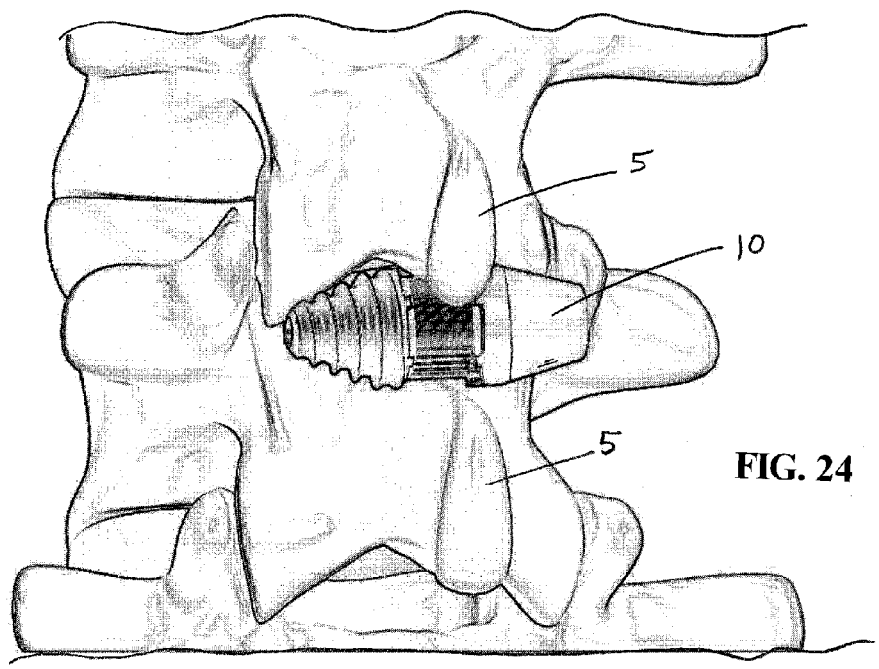
FIGS. 24-25 depict a perspective view of the implant of FIG. 1 shown in an implanted position.
Figure 25:
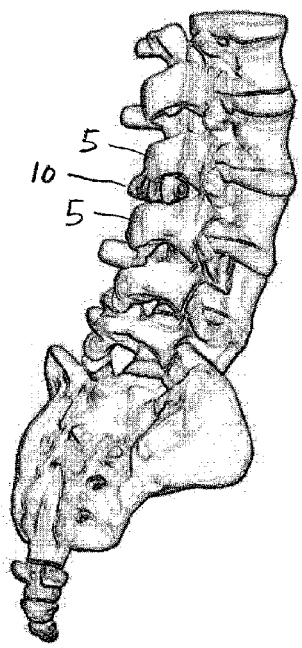

Referring to FIGS. 22-23, one exemplary embodiment of a method of installing implant 10 is shown. Implant 10 is advanced over guidewire 202 through cannulation 18 to the interspinous space 204. During lateral insertion of the implant between the spinous processes, one or more ramp surfaces or portions of the implant may contact one or both of the spinous processes 5 and may initially distract the processes. Implant 10 may be rotated to further advance implant 10 between the spinous processes and, the wedged or tapered shape of the distraction portion 20 may distract the spinous processes further apart from one another, until the implant is rotated and advanced laterally into an implanted position (FIGS. 22-25) with the distraction portion 20 positioned on the contralateral side of the spinous processes and the spinous processes are fitted into the central support portion 24 of the implant 10. Referring to FIGS. 24-25, once implant 10 is installed, the guidewire may be removed through the cannulation leaving the implant 10 in the interspinous space.

Figure 26:
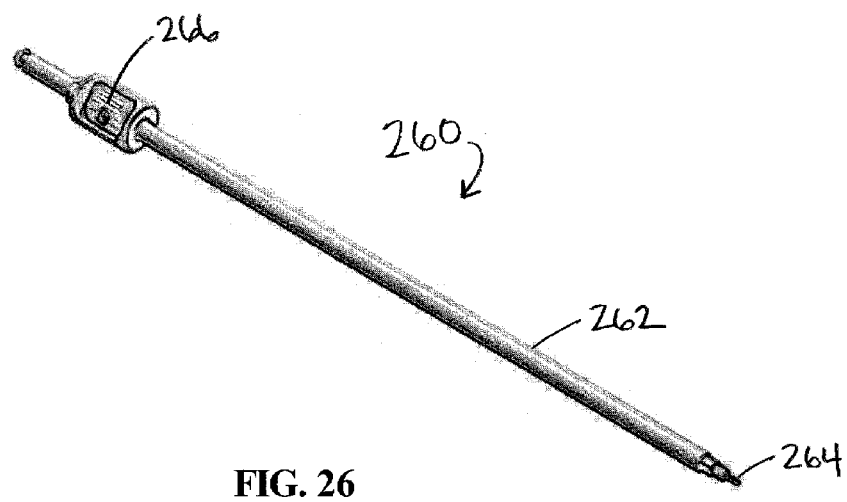
FIG. 26 is a perspective view of one embodiment of a removal tool according to the invention.

Referring to FIG. 26, one embodiment of an implant removal tool 260 is shown. Removal tool 260 generally comprises an elongate cannulated body 262 with an externally threaded distal tip 264 rotatably connected to thumb barrel member 266. Distal tip 264 is generally configured and dimensioned to engage threaded section 45, described above, of an implant to accommodate a threaded connection of removal tool 260 and an implant. In this regard, a surgeon may rotate distal tip 264 by rotating thumb barrel 266 to establish a threaded connection between the tool and the implant. As described above, such a threaded connection facilitates a laterally fixed relative connection between the implant and tool so that the implant does not dislodge from the trailing end and a surgeon may remove or back out the implant from the body if desired.

While the invention herein disclosed has been described by means of specific embodiments and applications thereof, numerous modifications and variations can be made thereto by those skilled in the art without departing from the scope of the invention.

What is claimed is:

1. A prosthetic device for implantation in the vertebral column, comprising:
    a body comprising a support portion extending laterally along a lateral axis between first and second end portions, the first end portion having a first end and a second end, the body defining a cannula extending therethrough along the lateral axis;
    wherein the first end portion has a tapering surface that extends along its longitudinal length from the second end to the first end;
    wherein at least a portion of the first end portion extends beyond the support portion in a direction perpendicular to the lateral axis;
    wherein the second end portion comprises a first section having a surface that extends linearly parallel to the lateral axis along its longitudinal length and a second section having a linear tapering surface that extends along its longitudinal length,
    wherein the device is configured and dimensioned to be inserted between adjacent spinous processes of the vertebral column in a lateral direction along the lateral axis and is advanceable over a guidewire extending through the cannula;
    wherein the first end portion comprises a ramp on at least a portion of an outer surface configured and dimensioned to engage and separate the adjacent spinous processes, the ramp increasing in diameter in a direction from a first end of the first portion to the support portion; and
    wherein the ramp comprises a grooved section having peaks extending along at least a portion thereof to rotatably advance the device in the lateral direction to position the support portion in a predetermined position between the spinous processes, wherein the grooved section comprises at least two peaks having different heights that extend along the lateral axis of the body,
    wherein the first end portion includes a plurality of wing members, the wing members being configured to be moveable from a first position to a second position, the wing members remaining below the peaks of the ramp in the first position and extending radially beyond the peaks in the second position, wherein the wing members each have a flat surface, wherein in the second position the flat surface is perpendicular to a longitudinal axis of the support portion, and
    wherein the wing members are biased toward the second position by an o-ring.

2. The device of claim 1, wherein at least a portion of the second end portion extends beyond the support portion in a direction perpendicular to the lateral axis.

3. The device of claim 2, wherein a portion of the end portions are configured and dimensioned to contact the lateral sides of the spinous process when the device is implanted in the vertebral column.

4. The device of claim 1, wherein the body is made from a polyetheretherketone (PEEK) material.

5. The device of claim 1, wherein the first end portion comprises a generally frustoconical shape.

6. The device of claim 1, wherein the ramp is helically shaped.

7. The device of claim 1, wherein the ramp is spiral shaped.

8. The device of claim 1, wherein the ramp is linearly shaped.

9. The device of claim 1, wherein the support portion is configured and dimensioned to fit between adjacent spinous processes and further comprises:
    a proximal support surface spaced longitudinally from a distal support surface by a first distance, the support surfaces configured to contact adjacent spinous processes of the vertebral column,
    wherein the first distance is predetermined for spacing of two adjacent spinous processes when the device is implanted in the vertebral column.

10. The device of claim 1, wherein the support portion has a generally circular cross-section.

11. The device of claim 1, wherein the body is made from a titanium material.

12. The device of claim 1, wherein the body is configured and dimensioned to be rotated in-situ to distract adjacent spinous processes.

13. The device of claim 1, wherein the body is maintained in an implanted position without additional fixation devices.

14. A prosthetic device for implantation in a treated area of an intervertebral space between vertebral bodies of a spine, comprising:
    a spacer body comprising a central support portion extending along a lateral axis between first and second end portions, the first end portion having a first end and a second end, the second end of the first end portion located proximate to the central support portion, the central support portion comprising a superior support surface and an inferior support surface and the first end portion comprising a superior end surface and an inferior end surface,
    wherein the first end portion has a tapering surface that extends along its longitudinal length from the second end to the first end, wherein the first end portion comprises a ramp including a grooved section having peaks extending along at least a portion thereof to rotatably advance the device in the lateral direction to position the central support portion in a predetermined position between the spinous processes, wherein the grooved section comprises at least two peaks having different heights that extend along the lateral axis of the spacer body,
    wherein the second end portion comprises a first section having a surface that extends parallel to the lateral axis along its longitudinal length and a second section having a linear tapering surface that extends along its longitudinal length,
    wherein the superior and inferior support surfaces of the central support portion each have a contact area capable of engaging with anatomy in the treated area and the superior and inferior surfaces are spaced apart a first distraction distance, wherein the superior and inferior end surfaces of the first end portion each have a contact area capable of engaging with anatomy in the treated area and the first and second surfaces of the first end portion are spaced apart a second distraction distance, wherein the first distraction distance is less than the second distraction distance, wherein when the device is in a first implantation position the adjacent vertebral bodies are maintained substantially separated by at least the second distraction distance and when the device is in a second implantation position the adjacent vertebral bodies are maintained substantially separated by at least the first distraction distance, and wherein the spacer body support portion is rotatable from the first implantation position to the second implantation position, wherein the central support is configured with a largest diameter that is less than a smallest diameter of the second end portion, wherein the first end portion includes a plurality of wing members, the wing members being configured to be moveable from a first position to a second position, the wing members remaining below the peaks of the ramp in the first position and extending radially beyond the peaks in the second position, wherein the wing members each have a flat surface, wherein in the second position the flat surface is perpendicular to a longitudinal axis of the support portion, and wherein the wing members are biased toward the second position by an o-ring.

15. The device of claim 14, wherein the first end portion is tapered along its longitudinal length.

16. The device of claim 14, wherein the body defines a cannula extending along the lateral axis through the body, the cannula configured and dimensioned for receiving a guidewire therethrough such that the device is rotatable and advanceable over the guidewire.

17. The device of claim 14, wherein in the second implantation position the first and second end portions are located laterally adjacent opposite lateral sides of a portion of the vertebral bodies.

18. The device of claim 14, wherein the spacer body is maintained in the second implantation position without additional fixation devices.

19. The device of claim 14, wherein the first end portion comprises an outer surface and, the first end portion further comprising a ramp portion along the outer surface.

20. A prosthetic device for implantation between adjacent spinous processes in the vertebral column, comprising:

an elongate body positioned between a first portion and a second portion, the first portion having a first end and a second end, wherein the first portion has a tapering surface that extends along its longitudinal axis from the second end to the first end, the width tapering from the second end, wherein the first portion is configured and dimensioned to contact a portion of the spinous processes and is rotatable with respect to the spinous processes to act or function as a cam to distract or separate the adjacent spinous processes, wherein the first portion comprises a ramp having a grooved section having peaks extending along at least a portion thereof to rotatably advance the device in the lateral direction to position the elongate body in a predetermined position between the spinous processes, wherein the grooved section comprises at least two peaks having different heights that extend along the lateral axis of the elongate body, wherein the second portion comprises a first section having a surface that extends linearly parallel to its longitudinal axis along its longitudinal length and a second section having a linear tapering surface that extends along its longitudinal length, wherein the first portion comprises a generally vertical wall section that is formed at the interface between the first portion and the elongate body, wherein after the device is implanted, the wall section serves to prevent dislodgement of the device from an interspinous space wherein the first portion includes a plurality of wing members, the wing members being configured to be moveable from a first position to a second position, the wing members remaining below the peaks of the ramp in the first position and extending radially beyond the peaks in the second position, wherein the wing members each have a flat surface, wherein in the second position the flat surface is perpendicular to a longitudinal axis of the support portion, and wherein the wing members are biased toward the second position by an o-ring.

21. The device of claim 20, wherein the body comprises cannula extending through the body along the lateral axis and wherein the device is configured and dimensioned to be inserted between adjacent spinous processes of the vertebral column in a lateral direction along the lateral axis and is advanceable over a guidewire extending through the cannula.

22. The device of claim 20, wherein the first portion comprises an outer surface and, the first end portion further comprising a ramp portion along the outer surface.

23. The device of claim 22, wherein the ramp is helically shaped.

24. The device of claim 23, wherein the ramp comprises a thread.

25. The device of claim 22, wherein the ramp is spiral shaped.

26. The device of claim 22, wherein the ramp is linearly shaped.

27. The device of claim 20, wherein the second portion comprises a flexible member extending around at least a portion of an exterior of the second portion to at least partially cushion the compression of adjacent spinous processes.

28. The device of claim 27, wherein the flexible member comprises a generally cylindrical sleeve made from a biocompatible polyurethane material.

* * * * *